United States Patent [19]

Kay

[11] 4,082,536
[45] Apr. 4, 1978

[54] HETEROCYCLIC COMPOUNDS AND THEIR USE AS PESTICIDES

[75] Inventor: Ian Trevor Kay, Wokingham, England

[73] Assignee: Imperial Chemical Industries Limited, London, England

[21] Appl. No.: 625,138

[22] Filed: Oct. 23, 1975

Related U.S. Application Data

[62] Division of Ser. No. 515,090, Oct. 15, 1974.

[30] Foreign Application Priority Data

Nov. 1, 1973 United Kingdom ............... 50827/73
Feb. 15, 1974 United Kingdom ................ 6959/74

[51] Int. Cl.$^2$ .............................................. A01N 9/22
[52] U.S. Cl. ........................................ 71/93; 424/249; 544/211; 544/194; 544/212
[58] Field of Search ............................ 71/93; 424/249

[56] References Cited

U.S. PATENT DOCUMENTS

| | | | |
|---|---|---|---|
| 3,855,219 | 12/1974 | Fuchs et al. | 71/93 X |
| 3,873,540 | 3/1975 | Fuchs et al. | 71/93 X |
| 3,901,682 | 8/1975 | Long | 71/93 |
| 3,902,887 | 9/1975 | Lin | 71/93 |
| 3,907,795 | 9/1975 | Tocker | 71/93 X |
| 3,907,796 | 9/1975 | Jewell et al. | 71/93 X |
| 3,933,815 | 1/1976 | Ploeg | 71/93 X |

*Primary Examiner*—Joseph Paul Brust
*Attorney, Agent, or Firm*—Cushman, Darby & Cushman

[57] ABSTRACT

Herbicidal and fungicidal triazinediones of the formula

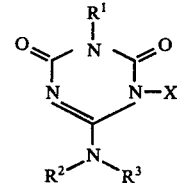

wherein R$^1$ is an aliphatic group, and either (a) R$^2$ is carboxylic acyl, or (b) R$^2$ is hydrogen or aliphatic and R$^3$ together with the group X forms a divalent radical Z linking the exocyclic nitrogen with the ring to form a second 5 or 6 membered heterocyclic ring, and X is hydrogen or an aliphatic radical, or together with R$^3$ forms the divalent group Z.

5 Claims, No Drawings

HETEROCYCLIC COMPOUNDS AND THEIR USE AS PESTICIDES

This is a division of application Ser. No. 515,090, filed Oct. 15, 1974.

This invention relates to heterocyclic compounds and chemical compositions containing them, and to their use as pesticides, more particularly as herbicides and fungicides.

According to the present invention, there are provided triazinedione compounds of the formula:

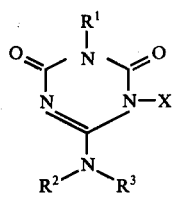

and salts thereof, wherein $R^1$ is an aliphatic radical and either (a) $R^2$ is a carboxylic acyl radical and $R^3$ is a hydrogen atom or an aliphatic radical, or (b) $R^2$ is a hydrogen atom or an aliphatic radical, and $R^3$, together with the group X, forms a divalent radical Z linking the nitrogen atom to which $R^3$ is attached to the nitrogen atom in the triazine ring, so as to form a second 5 or 6 membered heterocyclic ring; and X is a hydrogen atom or an aliphatic radical, or together with $R^3$ forms the divalent group Z.

By carboxylic acyl radical we mean an acyl radical derived from a carboxylic acid of the formula $R^4.CO_2H$ wherein $R^4$ represents a carboxy group, or an alkoxycarbonyl group, an aliphatic radical, a phenyl or substituted phenyl radical, or an alkoxy radical. Preferred acyl radicals include alkanoyl radicals of 2 to 8 carbon atoms, for example acetyl, propionyl, and butyryl radicals, and alkoxycarbonyl radicals of 2 to 8 atoms, for example methoxycarbonyl, ethoxycarbonyl, and propoxycarbonyl.

Preferred compounds according to the invention include those in which $R^1$ is an aliphatic radical of 1 to 20 carbon atoms. More preferably, $R^1$ is an alkyl radical of from 1 to 8 carbon atoms. Particularly preferred compounds include those in which that carbon atom of $R^1$ which is attached to the nitrogen atom is a secondary or tertiary carbon atom. A secondary carbon atom is one in which two of the valency links of the carbon atom are attached to other carbon atoms and a tertiary carbon atom is one in which three of the valency links of the carbon atom are attached to other carbon atoms. Examples of compounds containing a secondary carbon atom include those in which $R^1$ is an isopropyl or cyclohexyl radical. Examples of compounds in which $R^1$ contains a tertiary carbon atom include those in which $R^1$ is a tertiary butyl radical.

When $R^3$ is an aliphatic radical, it may be, for example, an alkyl radical, for example an alkyl radical of 1 to 6 carbon atoms.

When X is an aliphatic radical, it may be for example an alkyl radical of from 1 to 6 carbon atoms. When X is a hydrogen atom, the hydrogen is acidic, and the compounds will form salts with bases. Examples of such salts include alkali metal salts, for example lithium, sodium and potassium salts, alkaline earth metal salts, for example calcium and magnesium salts, ammonium salts, and salts formed from primary, secondary, or tertiary amines, for example primary, secondary and tertiary aliphatic amines in which the one, two or three aliphatic radicals each contain from one to six carbon atoms. Salts or compounds wherein X represents a hydrogen atom may in general be conveniently prepared simply by mixing the triazinedione compound with the stoichiometric proportions of an alkali metal hydroxide, alkaline earth metal hydroxide, ammonia, or amine, in a solvent or diluent. Water is generally the most convenient solvent or diluent for this purpose.

The divalent group Z in the compounds of the invention defined by the foregoing formula may have its valency links on two adjacent linked atoms, or on two atoms linked through a third atom, so that when linked to the triazine ring in the manner indicated above, it forms a second heterocyclic ring containing five or six ring atoms. The ring atoms of the group Z may be unsubstituted, as in the case when Z consists of a $-(CH_2)_2-$ or $-(CH_2)_3-$ group, or may bear various substituents. Thus, for example, the group Z may be an oxalyl group, $-CO.CO-$; or a 1,2-dihydroxyethylene group $-CH(OH)-CH(OH)-$ or a group of formula $-CH_2NR^5CH_2-$ where $R^5$ is a hydrocarbyl group of 1 to 10 carbon atoms, or hydrogen.

Examples of compounds of the invention are listed in Tables 1 and 2 below:

TABLE I

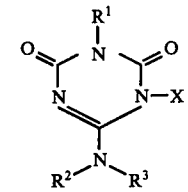

| Compound No. | $R^1$ | $R^2$ | $R^3$ | X | Melting point 20° C |
|---|---|---|---|---|---|
| 1 | $C_2H_5$ | H | $CH_3CO$ | H | 266 |
| 2 | $n.C_4H_9$ | H | $CH_3CO$ | H | 272 |
| 3 | $n-C_4H_9$ | $C_2H_5$ | $CH_3CO$ | H | 102–103 |
| 4 | iso-propyl | $C_2H_5$ | $CH_3CO$ | H | 123 |
| 5 | iso-propyl | $CH_3$ | $CH_3CO$ | H | 162–163 |
| 6 | iso-propyl | iso-propyl | $CH_3CO$ | H | 100–101 |
| 7 | iso-propyl | $CH_3$ | $C_2H_5CO$ | H | 113–114 |
| 8 | iso-propyl | $CH_3$ | $n.C_3H_7CO$ | H | 100–101 |
| 9 | iso-propyl | $CH_3$ | $(CH_3)_2.CH.CO$ | H | 81–82 |
| 10 | cyclohexyl | $CH_3$ | $CH_3CO$ | H | 176–177 |
| 11 | cyclohexyl | $CH_3$ | $C_2H_5CO$ | H | 147–148 |
| 12 | cyclohexyl | $CH_3$ | $HOOC.CO$ | H | 260 |
| 13 | $n.C_4H_9$ | $C_2H_5$ | $C_2H_5.CO$ | H | 114–115 |
| 14 | n. hexyl | $C_2H_5$ | $CH_3.CO$ | H | 98–99 |
| 15 | $n.C_4H_9$ | $n.C_4H_9$ | $CH_3.CO$ | H | 77–78 |
| 16 | $n.C_4H_9$ | $CH_3$ | $C_2H_5.CO$ | H | 92–93 |
| 17 | cyclo-hexyl | $C_2H_5$ | $CH_3CO$ | H | 191–192 |
| 18 | cyclo-hexyl | $CH_3$ | $CH_3CO$ | $CH_3$ | 99 |
| 19 | cyclo-hexyl | $C_2H_5$ | $CH_3CO$ | $CH_3$ | 99 |
| 20 | iso-propyl | $CH_3$ | $CH_3CO$ | $CH_3$ | 100–101 |
| 21 | cyclo-hexyl | H | $CH_3CO$ | $CH_3$ | 92–93 |
| 22 | cyclohexyl | H | $n.C_4H_9.CO$ | $CH_3$ | 71–72 |
| 23 | $n.C_4H_9$ | $C_2H_5$ | $n.C_3H_7.CO$ | H | 66–67 |
| 24 | $n.C_4H_9$ | $C_2H_5$ | $n.C_5H_{11}.CO$ | H | 49–51 |
| 25 | iso-$C_3H_7$ | $C_2H_5$ | $CH_3CO$ | $CH_3$ | Oil |
| 26 | iso-$C_3H_7$ | $CH_3$ | $C_2H_5OCO$ | H | 88–89 |
| 27 | iso-$C_3H_7$ | $CH_3$ | $C_6H_5CO$ | H | 124–125 |
| 28 | cyclohexyl | $CH_3$ | $n.C_3H_7.CO$ | H | 159–160 |
| 29 | cyclohexyl | $CH_3$ | $n.C_4H_9.CO$ | H | 179–180 |
| 30 | iso-$C_3H_7$ | $C_2H_5$ | $C_2H_5.CO$ | H | 88–90 |
| 31 | iso-$C_3H_7$ | $C_2H_5$ | $n.C_3H_7$ | H | 84–85 |
| 32 | iso-$C_3H_7$ | $n.C_3H_7$ | $n.C_3H_7.CO$ | H | 54–56 |
| 33 | iso-$C_3H_7$ | $n.$ | $CH_3CO$ | H | 89–90 |

TABLE I-continued

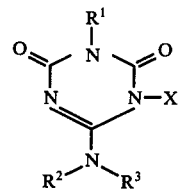

| Compound No. | R¹ | R² | R³ | X | Melting point 20° C |
|---|---|---|---|---|---|
| 34 | iso-$C_3H_7$ | n-$C_4H_9$ | n.$C_3H_7$.CO | H | Oil |
| 35 | cyclohexyl | $CH_3$ | $C_2H_5OCO$ | H | 151–152 |
| 36 | iso-$C_3H_7$ | $C_2H_5$ | $C_2H_5OCO$ | H | 75–77 |
| 37 | iso-$C_3H_7$ | $CH_3$ | $C_2H_5OCO.CO$ | $CH_3$ | 86 |
| 38 | cyclohexyl | n.$C_3H_7$ | $CH_3CO$ | H | 176 |

TABLE 2

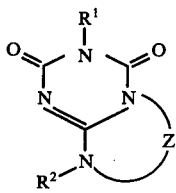

| Compound No. | R¹ | R² | Z | Melting Point °C |
|---|---|---|---|---|
| 39 | isopropyl | $C_2H_5$ | —CO—CO— | 218–220 |
| 40 | isopropyl | $CH_3$ | —CO—CO— | 224–225 |
| 41 | isopropyl | isopropyl | —CO—CO— | 208–209 |
| 42 | isopropyl | $CH_3$ | —(CH.OH)$_2$— | 158–160 |
| 43 | isopropyl | $CH_3$ | —CO—$CH_2$— | 211–213 |
| 44 | cyclohexyl | $CH_3$ | —(CH.OH)$_2$— | 269–270 |
| 45 | n-butyl | $C_2H_5$ | —(CH.OH)$_2$— | 164–165 |
| 46 | $C_2H_5$ | H | —(CH$_2$)$_3$— | 268 |
| 47 | n-$C_4H_9$ | H | —(CH$_2$)$_3$— | 272–273 |
| 48 | cyclohexyl | H | —(CH$_2$)$_3$— | 280 |
| 49 | isopropyl | $C_2H_5$ | —CH$_2$N(CH$_3$)—CH$_2$— | 173–175 |
| 50 | isopropyl | $C_2H_5$ | —CH$_2$N($C_4H_9$n).CH$_2$— | (liquid, $n_D^{20}$ 1.5200) |
| 51 | isopropyl | $CH_3$ | —CH$_2$N(CH$_3$).CH$_2$—— | 169–170 |
| 52 | isopropyl | isopropyl | —CH$_2$N(CH$_3$).CH$_2$— | 161–162 |
| 53 | n-$C_4H_9$ | $C_2H_5$ | —CH$_2$N(CH$_3$).CH$_2$— | 107–108 |
| 54 | iso-$C_3H_7$ | $CH_3$ | —CH$_2$CH$_2$— | 135–136 |
| 55 | cyclohexyl | $CH_3$ | —CH$_2$CH$_2$— | 192–193 |
| 56 | cyclohexyl | $CH_3$ | —CH$_2$N($C_6H_5$)CH$_2$— | 176 |
| 57 | iso-$C_3H_7$ | n.$C_3H_7$ | —CH$_2$N(CH$_3$)CH$_2$— | 168–170 |

The nuclear magnetic resonance spectrum of each of the compounds listed in Tables 1 and 2 was examined and found to be consistent with the structure given in the Tables.

In Table 2 above, Z (if unsymmetrical) is written anticlockwise, the left-hand valency bond being linked to the nitrogen atom which carries R².

In a further aspect, the invention provides a process of inhibiting the growth of unwanted plants, which comprises applying to the plants, or to a plant growth medium, a phytotoxic amount of a triazinedione compound of the formula:

wherein R¹, R², R³ and X are as previously defined. Preferred compounds for use in the herbicidal process of the invntion include those in which R¹ is an alkyl radical of 1 to 6 carbon atoms, R² is a carboxylic acyl group, R³ is an aliphatic radical, and X is hydrogen or an aliphatic radical of 1 to 6 carbon atoms, for example methyl. Another group of preferred compounds are those in which R¹ is an alkyl radical of 1 to 6 carbon atoms, R² is an aliphatic radical of 1 to 6 carbon atoms, and R³ together with X forms a divalent radical Z linking the nitrogen atom to which R³ is attached to the nitrogen atom in the triazine ring so as to form a second 5- or 6- membered heterocyclic ring.

The rate at which compounds are applied in accordance with the herbicidal process of the invention will depend upon a number of factors, for example the identity of the plants whose growth is to be inhibited, and the particular compound selected for application, but in general a rate of from 0.1 to 10 kilograms per hectare is suitable, while from 0.5 to 5 kilograms per hectare is preferred. The post-emergence activity of the compounds is often higher than their pre-emergence activity.

The compounds have been found to be generally less phytotoxic to maize than to many other plant species, and by application at a suitable rate, the compounds may be used selectively to control weeds in maize crops. Accordingly, in a further aspect, the invention provides a process of inhibiting the growth of weeds in crops of maize, which comprises applying to the crop area a triazinedione compound of the formula:

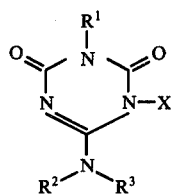

wherein $R^1$, $R^2$, $R^3$ and X are as hereinbefore defined, in an amount sufficient to inhibit the growth of weeds but insufficient substantially to damage the maize.

Preferred compounds for use in selectively controlling weeds in maize crops include those in which the group $R^1$ is an alkyl group of 1 to 8 carbon atoms. Preferably $R^2$ is a carboxylic acyl group of 2 to 5 carbon atoms and the group $R^3$ is a hydrogen atom or a methyl group; or alternatively, $R^2$ may be an alkyl group of 1 to 4 carbon atoms and $R^3$ may be a group Z as hereinbefore defined.

Certain compounds of the invention are active against plant fungal diseases at rates of application lower than those at which they cause substantial damage to plants. The invention therefore further provides a process of combatting plant fungal diseases by applying to plants, or to plant growth media, a fungicidal but substantially non-phytotoxic quantity of a compound according to the invention. Preferred compounds for this use are those in which $R^1$ is an aliphatic group of 2 to 6 carbon atoms. Particularly preferred compounds are those in which $R^1$ is a butyl group. Preferably, $R^2$ is an alkanoyl radical of 2 to 4 carbon atoms, and $R^3$ is an alkyl group of 1 to 4 carbon atoms.

The compounds of the invention are particularly effective against powdery mildew infestations of cereal plants (for example barley), apples, and vines. The rate at which the compounds are applied when used as fungicides will depend upon factors such as the disease to be controlled, the compound chosen for use, and the tolerance of the host plants to the herbicidal action of the compound chosen for use, but a rate of between 0.05 and 5 kilograms per hectare, preferably between 0.1 and 2 kilograms per hectare will generally be suitable.

The fungicidal activity of the compounds of the invention is typically found to be systemic. That is to say, the chemicals do not combat fungal attack merely at the site at which they come into contact with the plants, but are taken up into the plant and transported to other parts of the plant where they can combat fungal attack. The fungicidal effect is generally highly specific. Thus, for example, compound No. 3 of Table I is active against powdery mildews of wheat and barley (*Erysiphe graminis*) and downy mildew and powdery mildew of vine, but is much less active against most other foliar fungal diseases. Certain compounds of the invention are also active against plant bacterial diseases.

The compounds used in the process of the invention are preferably applied to plants in the form of a composition in which the active ingredient is mixed with a diluent or carrier. Preferably the composition also comprises a surface-active agent to assist in spreading the composition over the surface of plants to which it is applied.

Compositions according to the invention may be solid or liquid, and include both dilute and concentrated compositions which require to be diluted before use.

Preferably the compositions contain from 0.01 to 90% by weight of the triazinedione used as active ingredient. Dilute compositions ready for use preferably contain from 0.01 to 2% of the active ingredient, while concentrated compositions may contain from 20 to 90% of active ingredient, although from 20 to 70% is usually preferred.

Solid compositions may be in the form of a powder, in which the active ingredient is mixed with a powdered solid diluent. Suitable solid diluents include for example, Fuller's earth, powdered kaolin, gypsum, chalk and kieselguhr. Such solid compositions may be applied as foliar dusts, or (for fungicidal purposes) as seed dressings.

Liquid compositions may comprise a solution or dispersion of an active ingredient in water optionally containing a surface-active agent, or may comprise a solution or dispersion of an active ingredient in an organic diluent, which may optionally contain a surface-active agent. Another form of liquid compositions comprises a solution of an active ingredient in a water-immiscible organic solvent which is dispersed as droplets in water.

Examples of surface-active agents which may be used in the compositions of the invention include the products of condensation of ethylene oxide with the following substances: alkyl substituted phenols such as octyl phenol and nonylphenol; sorbitan monolaurate; oleyl alcohol; and propylene oxide polymer. A particular example od such a condensation product is the substance sold under the name of "Lissapol" (Lissapol" is a Trade Mark). Other satisfactory surface-active agents include calcium dodecylbenzenesulphonate, and calcium, sodium and ammonium lignosulphonates. The amount of surface-active agent included in the compositions of the invention may vary, as will be evident to those skilled in the art, but from 0.1 part to 0.5 part by weight per part of triazine dione compound is often suitable.

A preferred form of concentrated composition comprises the active ingredient which has been finely divided and which has been dispersed in water in the presence of a surface-active agent and a suspending agent. Preferred suspending agents are those which impart thixotropic properties to, and increase the viscosity of the concentrate. Examples of preferred suspending agents include hydrated colloidal mineral silicates, such as montmorillonite, beidellite, hectorite and saucorite. Bentonite is especially preferred. Other suspending agents include cellulose derivatives and polyvinyl alcohol.

Compounds according to the invention may be prepared in a variety of ways. Compounds in which $R^2$ is a carboxylic acyl group and $R^3$ is a hydrogen atom or an aliphatic radical may be prepared, for example, by reacting a triazinedione compound in which $R^2$ is a hydrogen atom with a carboxylic acylating agent, for example a carboxylic acid chloride or carboxylic acid anhydride, as in the following scheme:

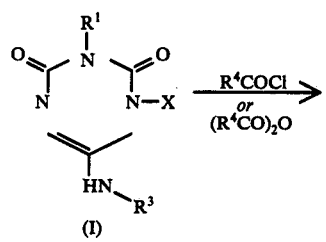

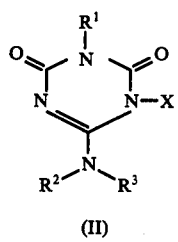

In the above scheme, $R^3$ and X each stand for a hydrogen atom or an aliphatic radical, and $R^1$ and $R^4$ are as previously defined.

Compounds of formula (I) are in general already known, having been described for example in Belgian Pat. No. 799,932 and Belgian Pat. No. 806,964. Methods for production of (I) are therefore already known. The present invention, however, further provides novel methods of preparing both the acylaminotriazinediones and the aminotriazinediones (I) from which they may be prepared. Three methods A, B and C are described below for preparing aminotriazinediones; these methods can be used to prepare compounds of formula (I) above, which may then be acylated.

METHOD A

In this method, a guanidine derivative of formula

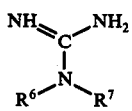

wherein $R^6$ and $R^7$ may each be a hydrogen atom or an aliphatic radical, is reacted with a chloroformic ester $ClCO_2R^8$, wherein $R^8$ is a hydrocarbyl group, preferably an alkyl group of 1 to 6 carbon atoms, for example methyl or ethyl, or preferably with a dialkylcarbonate $(R^8O)_2CO$ to give an intermediate (III). This is then further reacted with an isocyanate $R^1NCO$ wherein $R^1$ has any of the meanings hereinbefore assigned to it. The reaction product so obtained cyclises to a triazinedione compound, as shown in the scheme below:

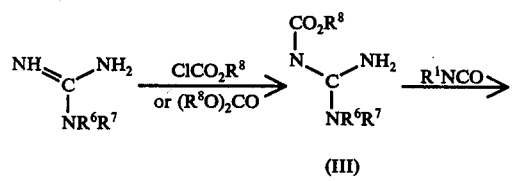

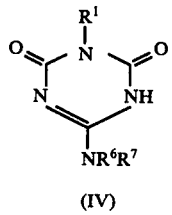

The conversion of (III) to (IV) may be carried out in the presence of a catalytic amount of a tertiary amine, preferably a trialkylamine in which each of the three alkyl groups contains 1 to 6 carbon atoms.

The reaction of the chloroformic ester $ClCO_2R^8$ with the guanidine may be carried out in water. Alternatively the preparation of the ethoxycarbonyl guanidine may be carried out by reacting diethylcarbonate with the free guanidine base in ethanol solution. In this method the free guanidine is preferably prepared in ethanol by adding 1 molar proportion of sodium ethoxide to a guinidine salt in ethanol.

METHOD B

This method is based upon the discovery that certain triazinone ethers are converted into triazine diones by heating, as shown in the following scheme:

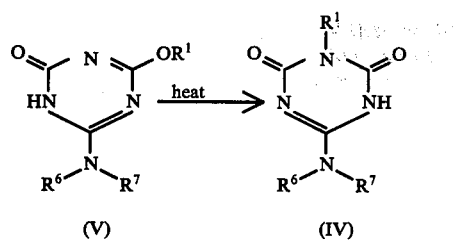

In the foregoing scheme, $R^1$, $R^6$ and $R^7$ have the meanings previously assigned to them.

The triazinone ethers (V) required as starting materials in the above scheme may be prepared in the following alternative ways:

(a) An alkyl ester of an alkoxy(thionocarbonyl) carbamic acid (VI) is converted into an S-alkyl derivative (VII) and the latter is then reacted with a guanidine derivative to give a triazinone ether (V) according to the following scheme:

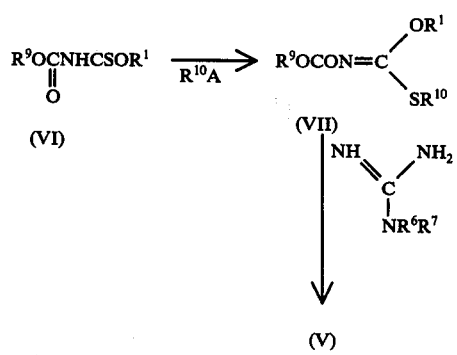

In the foregoing scheme, $R^1$, $R^6$, and $R^7$ have the meanings previously ascribed to them, while $R^9$ represents an alkyl radical, preferably of 1 to 4 carbon atoms, $R^{10}A$ represents an alkylating agent, $R^{10}$ being an alkyl group, preferably of 1 to 6 carbon atoms. The alkylating agent may be an alkyl halide, for example methyl or ethyl iodide, or a dialkyl sulphate, for example dimethyl or diethyl sulphate. The alkyl alkoxy (thionocarbonyl) carbamates (VI) used as starting materials are themselves a known class of compounds, having been described, for example, by R E Doran, in the Journal of the Chemical Society for 1896 at page 324.

(b) In an alternative method of preparing the triazinone ethers (V), the starting material is cyanuric chloride. The cyanuric chloride is first treated with an amine $R^6R^7NH$, preferably in the presence of an acid binding agent, and the aminotriazine (VIII) so obtained is then reacted with a metal derivative $R^1OM$ of an alcohol $R^1OH$ to give the triazine ether (IX). This is then converted into the triazinone ether (V) by reaction with formic acid. The reaction scheme is shown below:

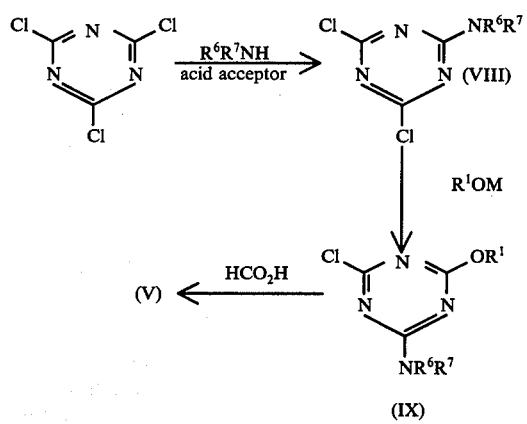

The conversion of (IX) to (V) with formic acid proceeds smoothly, although it was found extremely difficult to remove the chlorine atom from (IX) by hydrolysis with aqueous alkali. The acid acceptor mentioned in the foregoing scheme may be for example a primary, secondary, or tertiary amine or may be an alkali metal carbonate or hydroxide.

METHOD C

In this method, aminotriazinediones are prepared by heating an S-substituted mercapto triazine dione (X) with a carboxylic acid addition salt of an amine $R^6R^7NH$ as shown in the scheme below:

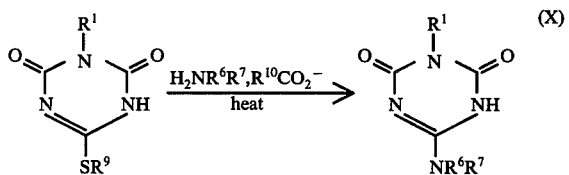

In the above scheme, the symbols $R^1$, $R^6$, $R^7$, $R^9$, and $R^{10}$, have the values previously assigned to them.

The S-substituted mercapto compounds are known compounds.

The ring NH group in the 4-alkylthio compounds (X) may readily be alkylated by treatment with an alkylating agent such as for example an alkyl halide or a dialkyl sulphate, in the presence of a base. Compounds according to the invention wherein the group X is an aliphatic radical may therefore be prepared by method C, by alkylating a compound of formula (X) above with the appropriate alkylating agent, then heating the alkylated compound with an amine salt to convert it to the corresponding 4-amino derivative, and finally acylating the latter to obtain the compounds of the invention. The scheme is illustrated by the following scheme:

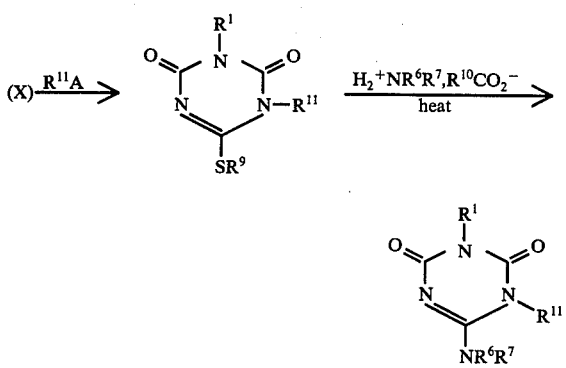

In the above scheme $R^1$, $R^6$, $R^7$, $R^9$, and $R^{10}$ each have the meanings previously assigned to them and $R^{11}A$ is an alkylating agent in which $R^{11}$ is an alkyl group of from 1 to 6 carbon atoms.

Examples of alkylating agents include alkyl halides and dialkyl sulphates.

Compounds according to the invention wherein the group $R^2$ is —$CO.CO_2H$, that is to say, oxalamides may be prepared by hydrolysis of compounds in which Z is —CO.CO— (the preparation of these compounds is described below). Compounds in which the group $R^2$ is —$CO.OR^8$ may be prepared by acylation of the appropriate aminotriazineedione with a chloroformic ester $Cl.CO.OR^8$.

Compounds in which Z is —CO.CO— tend to hydrolyse in water to form compounds in which X is H and $R^2$ is —$CO.CO_2H$. The rate of hydrolysis varies from one compound to another.

Compounds in which Z is —$CO.CH_2$— are made by condensation of the corresponding triazine diones in which $R^3$ is H with chloracetic anhydride; compounds in which Z is —CH(OH).CH(OH)— by condensation of the corresponding triazine dione in which $R^3$ is H with glyoxal. Compounds in which Z is —$CH_2NR^5CH_2$— ($R^5$ being hydrogen or an aliphatic alicyclic or aromatic hydrocarbon of 1 to 10, preferably containing not more than six carbon atoms) are prepared by reaction of the corresponding triazine dione in which $R^3$ is H with formaldehyde and a primary amine of formula $R^5NH_2$. Compounds in which Z is (—$CH_2$)$_n$— ($n=2$ or 3) may be prepared by Method A, using the appropriate cyclic guanidine as in Example 7.

EXAMPLE 1

This Example illustrates the preparation of compounds according to the invention and as listed in Table I, with the exception of compound no. 12.

Compound no. 3 of Table I was prepared by heating 1-n-butyl-4-ethylaminotetrahydro-1,3,5-triazine-2,6-dione (formula I, $R^1=C_4H_9$, $R^3=C_2H_5$, X=H) (2.12 g.) and acetic anhydride under reflux for 2 hours. Removal of the excess of acetic anhydride under reduced pressure followed by crystallisation of the residue from chloroform-hexane gave the product as colourless needles, m.p. 102°–103° C.

The remaining compounds of Table 2, except no. 12 were prepared by similar methods, starting from the appropriate 4-amino-1,3,5-triazine-2,6-dione derivative and the appropriate acid anhydride or acid chloride.

The 4-amino-1,3,5-triazine-2,6-dione derivatives were prepared by Methods A and C. By way of an example of Method A, the preparation of 4-dimethylamino-1-ethyl-tetrahydro-1,3,5-triazine-2,6-dione (formula IV, $R^1=C_2H_5$, $R^6=R^7=CH_3$) is described.

(a) Preparation of carbamate intermediate

N,N-dimethylguanidine hydrochloride (123.5 g; 1M) was added to a solution of potassium hydroxide (112.2 g; 2M) in water (ca. 300 ml.). The solution was stirred and kept at $-10°$ C to $-5°$ C by cooling while ethyl chloroformate (108.5 g; 1M) was added over a period of 45 minutes. After addition was complete, the solution was allowed to warm to room temperature, the water was evaporated in a vacuum, and the residue was extracted with boiling chloroform (300 ml.). The extracts were cooled, dried, and evaporated to yield a yellow oily solid. Recrystallisation from a 2:1 mixture of toluene and petroleum (b.p. 40°–60° C) gave the white crystalline carbamate derivative (formula III, $R^8=C_2H_5$, $R^6=R^7=CH_3$) having a melting point of 73°–76° C.

(b) Preparation of Triazinedione

The carbamate derivative so obtained was dissolved in dry toluene (ca. 100 ml. per 15 g. of carbamate) and heated under reflux with ethyl isocyanate (1 molar proportion) and a little dry triethylamine as catalyst for 16 hours. The toluene was then removed in a vacuum and the residue recrystallised from ethanol, giving the triazine dione as a white fibrous solid of melting point 236°–238° C.

Using the appropriate guanidine starting material and aliphatic isocyanate the following 4-aminotriazinediones were prepared by the procedure of Method A.

TABLE 3

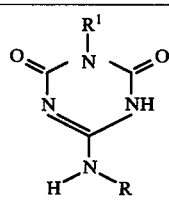

| $R^1$ | R | Melting Point ° C |
|---|---|---|
| $C_4H_9$ | $C_2H_5$ | 244 |
| iso $C_3H_7$ | $C_2H_5$ | 228 |
| iso $C_3H_7$ | $CH_3$ | 280–282 |
| iso $C_3H_7$ | iso $C_3H_7$ | 235–237 |
| n hexyl | $C_2H_5$ | 218–220 |
| n $C_4H_9$ | n $C_4H_9$ | 247–248 |
| n $C_4H_9$ | $CH_3$ | 241–242 |
| $C_2H_5$ | H | |
| $C_4H_9$ | H | |

Further 4-aminotriazinediones were prepared by Method C, that is to say by reaction of an appropriately 1-substituted -4-methylthio-tetrahydro-1,3,5-triazine-2,6-dione with the carboxylic acid salt of the appropriate amine. As an example of Method C, the following is a description of the preparation of 1-cyclohexyl-4-methyl-amino-tetrahydro-1,3,5-triazin-2,6-dione.

A mixture of 1-cyclohexyl-4-methylthio-tetrahydro-1,3,5-triazine-2,6-dione (24.1 g.) and methylammonium acetate (45.5 g.) was heated to 150° C for 3 hours. After allowing the mixture to cool, water (200 ml.) was added and the product, 1-cyclohexyl-4-methylamino-tetrahydro-1,3,5-triazin-2,6-dione separated. It was washed with water, dried, and recrystallised from aqueous dimethylformamide to give colourless needles, (21.0 g, 95%) m.p. 299°–300° C (with decomposition). The compounds in the following table were prepared in the same way.

TABLE 4

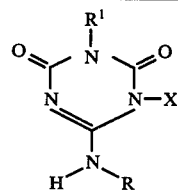

| $R^1$ | R | X | Melting Point ° C |
|---|---|---|---|
| cyclohexyl | $CH_3$ | H | 299–300 |
| cyclohexyl | $C_2H_5$ | H | 257–259 |
| cyclohexyl | $CH_3$ | $CH_3$ | 262 |
| cyclohexyl | $C_2H_5$ | $CH_3$ | 214 |
| iso $C_3H_7$ | $CH_3$ | $CH_3$ | 224 |
| cyclohexyl | H | $CH_3$ | 287–288 |
| iso $C_3H_7$ | $C_2H_5$ | $CH_3$ | 193 |
| iso $C_3H_7$ | n $C_3H_7$ | H | 107–108 |
| iso $C_3H_7$ | n $C_4H_9$ | H | 98–99 |
| cyclohexyl | n $C_3H_7$ | H | 237–238 |

EXAMPLE 2

This Example illustrates the preparation of compound no. 43 of Table 2.

A mixture of 1-isopropyl-4-methylamino-tetrahydro-1,3,5-triazin-2,6-dione (1.84 g.) and chloroacetic anhydride (7.5 g.) was heated at 130° for 2–5 hours. Trituration of the residue with hexane gave a solid which was separated and washed with hexane. Crystallisation of the solid from dichloromethane/ether gave the product as colourless needles (1.48 g.) m.p. 211°–213° C.

EXAMPLE 3

This Example illustrates the preparation of compound no. 12 of Table 1.

A mixture of 1-cyclohexyl-4-methylamino-tetrahydro-1,3,5-triazine-2,6-dione (2.84 g.) and oxalyl chloride (4.0 ml.) in anhydrous toluene (40 ml.) was heated under reflux for 3 hours. The resulting mixture was shaken with water. Compound no. 12 was recovered and had a melting point of 260° after recrystallisation.

EXAMPLE 4

This Example illustrates the preparation of compound no. 40 of Table 2.

A mixture of 1-isopropyl-4-methylamino-tetrahydro-1,3,5-triazine-2,6-dione (2.76 g.) and oxalyl chloride (3.9 ml.) in anhydrous toluene (40 ml.) was heated under reflux for 3 hours. Removal of the toluene under reduced pressure and crystallisation of the residue from acetone/light petroleum gave the product (2.7 g.) as colourless crystals, m.p. 224°–225° C. Using the appropriate 4-amino triazine derivative and oxalyl chloride, the following compounds of Table 2 were prepared by the same method: 39 and 41.

EXAMPLE 5

This Example illustrates the preparation of Compound no. 45 of Table 2.

A mixture of 1-n-butyl-4-ethylamino-tetrahydro-1,3,5-triazin-2,6-dione (2.12 g.) and glyoxal hydrate (0.84 g.) in ethanol (80 ml.) was heated under reflux for 3 hours. Following the removal of the ethanol under reduced pressure, the residual gum was taken up in ether and filtered to remove insoluble material. Evaporation of the ether and crystallisation of the residue from water gave the product (1.2 g.) as colourless crystals, m.p. 164°-166° C.

Compounds 42 and 44 of Table 2 were so prepared.

EXAMPLE 6

This Example illustrates the preparation of Compound no. 53 of Table 2.

To a solution of 1-n-butyl-4-ethylamino-tetrahydro-1,3,5-triazin-2,6-dione (2.12 g.) in boiling ethanol (70 ml.) was added an aqueous solution of formaldehyde (1.5 ml; 40% w/v), and following the addition the mixture was allowed to cool for 30 minutes. Methylamine (1.24 ml; 25% w/v aqueous) was then added and the mixture heated under reflux for a further 1 hour. Following the removal of solvent, the residue was taken up into chloroform which was washed with aqueous sodium hydroxide (50 ml; 5%). The chloroform layer was dried ($NaSO_4$) and evaporated and the residue crystallised from methylene chloride-n-hexane-ether at $-60°$ C to give the product (1.3 g.) as colourless crystals, m.p. 107°-108° C.

By the same technique compounds 50, 51, 52 and 57 of Table 2 were prepared.

EXAMPLE 7

This Example illustrates the preparation of Compound no. 54 of Table 2.

A mixture of ethyl hexahydropyrimidin-2-ylidenecarbamate (1.71 g.) (prepared as described by Kay et al., J. C. S. Perkin I, 2644 (1973)) and ethyl isocyanate (0.71 g.) in anhydrous toluene (15 ml.) was heated under reflux for 16 hours. Removal of the toluene under reduced pressure and crystallisation of the residue from water gave the product (1.1 g.) as colourless crystals, m.p. 268° C.

Compounds 55 and 56 of Table 2 were prepared by the same technique, using the appropriate starting materials.

EXAMPLE 8

This Example illustrates the preparation of 1-ethyl-4-dimethylamino-tetrahydro-1,3,5-triazin-2,6-dione by Method B, starting with cyanuric chloride.

(a) Preparation of 2,4-dichloro-6-dimethylamino-1,3,5-triazine

A suspension of cyanuric chloride (27.6 g.) in anhydrous ether (600 ml.) was kept at $-30°$ C and treated with dimethylamine (13.5 g.). Following the addition the mixture was allowed to warm to 0° C and poured on to ice. The ether layer was separated, dried, and evaporated and the residue crystallised from light petroleum to give the product (26.0 g.) having a melting point of 123°-124° C.

(b) 2-Chloro-4-ethoxy-6-dimethylamino-1,3,5-triazine

A solution of sodium (0.46 g.) in ethanol (50 ml.) was added with stirring and waterbath cooling (25° C) to a solution of the dichlorotriazine (3.86 g.) from (a) in ethanol (50 ml.). Following the addition the solution was poured into ice water (250 ml.) and the product collected, dried and crystallised from petroleum as needles (2.5 g.) having a melting point of 124° C.

(c) 4-Dimethylamino-2-ethoxy-1,3,5-triazine-6-one

The chlorotriazine from (b) (1.2 g.) was heated in formic acid (15 ml.) on a steam bath for 45 minutes, when gas evolution had ceased. The excess of formic acid was removed under reduced pressure and the residue was dissolved in the minimum amount of water, which was brought to pH 6-7 by adding solid sodium bicarbonate. The solution was extracted with chloroform and the extracts dried and evaporated. The residue crystallised from ethanol to give the product (1.1 g.) having a melting point of 215°-216° C. (The melting point sample resolidified and re-melted at 235° C).

(d) 4-Dimethylamino-1-ethyl-1,3,5-triazine-2,6-dione

The triazinone from (c) (0.5 g.) was heated in an oil bath at 220° C for 10 minutes. The cooled product was recrystallised from ethanol to give the triazine-dione having a melting point of 233°-235° C. (decomp.).

EXAMPLE 9

This Example illustrates an alternative preparation of 4-dimethylamino-6-ethoxy-1,3,5-triazin-2-one (formula V, $R^6=R^7=CH_3$), for which a preparation has already been described in Example 8.

(a) Preparation of Ethyl-N-(Ethoxy(methylthio)methylene) carbamate (formula VIII, $R^1=C_2H_5$, $R^9=C_2H_5$, $R^{10}=CH_3$).

Ethyl ethoxythiocarbonylcarbamate (1 molar proportion) was added to a stirred solution of potassium carbonate in water (10 ml. per gram of carbamate). After 15 minutes stirring, the solution was filtered and dimethyl sulphate added dropwise to the filtrate with vigorous stirring over 45 minutes. The mixture was then stirred for 1 hour and extracted with light petroleum. The extracts were dried and cooled to $-40°$ C., when the carbamate separated. Recrystallised from petroleum, the carbamate had a melting point of 38°-39° C.

(b) N,N-Dimethylguanidine hydrochloride (3.23 g; 0.026 mol.) was added to a solution of sodium (0.61 g; 0.026 mol.) in anhydrous ethanol (50 ml.) and the mixture was heated under reflux for 30 minutes. The carbamate prepared in (a) above (5.0 g., 0.026 mol.) was then added and the mixture heated under reflux for 22 hours. The ethanol was removed, water (75 ml.) added, and the pH of the solution adjusted to 6 to 7 with acetic acid. The product was collected, washed with water, and recrystallised from ethanol to give 4-dimethylamino-6-ethoxy-1,3,5-triazin-2-one.

EXAMPLE 10

This Example illustrates the preparation of Compound no. 54 of Table 2.

1-Isopropyl-4-(N-2-hydroxyethyl-N-methyl-)aminotetrahydro-1,3,5-triazine-2,6-dione (1.5 g.), suspended in anhydrous tetrahydrofuran (20 ml.), was treated with thionyl chloride (5 ml.). Following the mildly exothermic reaction the solution was allowed to cool to room temperature and then evaporated. The residual solid was taken in in water (50 ml.) which was then brought to pH 7 by addition of solid sodium bicarbonate and extracted with chloroform (4 × 20 ml.). Evaporation of the extracts followed by crystallisation of the residue from carbon tetrachloride gave the product (1.0 g.) having a melting point of 135°-136° C.

The starting material for this preparation was obtained by treating the known compound 1-isopropyl-4-methylthiotetrahydro-1,3,5-triazine-2,6-dione with the acetate salt of N-methyl ethanolamine according to Method C, and was used directly without further purification for the preparation of compound 54. Compound 55 was prepared in a similar way.

EXAMPLE 11

This Example illustrates the herbicidal properties of compounds used in the process of the invention. Each compound (0.12 g.) was formulated for test by mixing it with 5 ml. of an emulsion prepared by diluting 100 ml. of a solution containing 21.8 grams per liter of Span 80 and 78.2 grams per liter of Tween 20 in methyl cyclohexanone to 500 ml. with water. "Span" 80 is a Trade Mark for a surface-active agent comprising a condensate of sorbitan monolaurate with 20 molar proportions of ethylene oxide. The mixture of the compound and the emulsion was shaken with glass beads and diluted to 12 ml. with water.

The spray composition so prepared was sprayed on to young pot plants (post-emergence test) of the species named in Table 5 below, at a rate equivalent to 1000 liters per hectare (10 kilograms of pyrimidine compound per hectare). Damage to plants was assessed 14 days after spraying by comparison with untreated plants, on a scale of 0 to 3 where 0 is no effect and 3 represents 75 to 100% kill. In a test for pre-emergence activity, seeds of the test species were placed on the surface of fiber trays of soil and were sprayed with the compositions at the rate of 1000 liters per hectare. The seeds were then covered with further soil. Fourteen days after spraying, the seedlings in the sprayed fiber trays were compared with those in unsprayed control trays, the damage being expressed on the same scale of 0 to 3. The results are given in Table 5 below. It should be noted that the kill of plants in these tests is not necessarily complete after 14 days. Plants appearing healthy at this time may die subsequently, particularly in the pre-emergence test.

TABLE 5

| Compound No. | Pre-emergence | | | | | | Post-emergence | | | | | |
|---|---|---|---|---|---|---|---|---|---|---|---|---|
| | Le | To | Cl | Wh | Dg | Pr | Le | To | Cl | Wh | Dg | Pr |
| 6 | 0 | 0 | 0 | 0 | 0 | 0 | 0 | — | 0 | 2 | 3 | 2 |
| 13 | 0 | 0 | 0 | 0 | 0 | 0 | 0 | 2 | 1 | 0 | 0 | 0 |
| 14 | 0 | 0 | 0 | 1 | 0 | 0 | 0 | 3 | 0 | 0 | 0 | 0 |
| 15 | 0 | 0 | 0 | 0 | 0 | 0 | 2 | 3 | 1 | 0 | 0 | 0 |
| 21 | 0 | 0 | 0 | 0 | 1 | 0 | 1 | 3 | 2 | 0 | 1 | 0 |
| 22 | 1 | 1 | 1 | 0 | 0 | 0 | 1 | 3 | 2 | 1 | 1 | 0 |
| 23 | 0 | 0 | 0 | 0 | 2 | 0 | 0 | 1 | 1 | 0 | 0 | 0 |
| 24 | 1 | 0 | 0 | 0 | 1 | 0 | 0 | 2 | 2 | 0 | 0 | 0 |
| 33 | 0 | 0 | 0 | 0 | 0 | 0 | 0 | 1 | 1 | 0 | 2 | 0 |
| 34 | 0 | 0 | 0 | 0 | 0 | 2 | — | 0 | 0 | 1 | 0 | 0 |
| 36 | 0 | 0 | 0 | 0 | 0 | 0 | 0 | 2 | 2 | 1 | 2 | 0 |
| 37 | 1 | 1 | 1 | 0 | 2 | — | 3 | 3 | 3 | 1 | 3 | 2 |
| 41 | 0 | 0 | 0 | 0 | 0 | 0 | 2 | — | 3 | 0 | 2 | 1 |
| 56 | 2 | 1 | 2 | 0 | 2 | 0 | 3 | 3 | — | 1 | 2 | 0 |

The names of the test plants are as follows:-
Le - Lettuce
To - Tomato
Cl - Clover
Wh - Wheat
Dg - *Digitaria sanguinalis*
Pr - Perennial rye grass

EXAMPLE 12

This Example further illustrates the herbicidal properties of compounds according to the invention. For this test, each compound was formulated by mixing it with 5 ml. of an emulsion prepared by diluting 160 ml. of a solution containing 21.8 g. per liter of Span 80 and 78.2 g. per liter of Tween 20 in methylcyclohexanone to 500 ml. with water. The 5 ml. of emulsion containing the test compound was then diluted to 40 ml. with water and sprayed on to the range of test species in Table 6 as described for Example 11. Damage to the test plants was assessed on a scale of 0 to 5 where 0 is no effect and 5 is complete kill.

The names of the test plants are as follows:

| | | | |
|---|---|---|---|
| Sb - | Sugar beet | Po - | *Potulaca oleracea* |
| Rp - | Rape | Mz - | Maize |
| Ct - | Cotton | Br - | Barley |
| P - | Pea | Rc - | Rice |
| SN - | *Senecio vulgaris* | Ot - | Oat |
| Ip - | *Ipomoea purpurea* | Dg - | *digitaria sanguinalis* |
| Am - | *Amaranthus retroflexus* | | |
| Pa - | *Polygonum aviculare* | El - | *Eleusine indica* |
| Ca - | *Chenopodium album* | Pn - | *Poa annua* |

TABLE 6

| Compound No. | Pre or Post Emergence | Rate kg/ hectare | Test Plants | | | | | | | | | | | | | | | |
|---|---|---|---|---|---|---|---|---|---|---|---|---|---|---|---|---|---|---|
| | | | Sb | Rp | Ct | P | Sn | Ip | Am | Pa | Ca | Po | Mz | Br | Rc | Ot | Dg | El | Pn |
| 3 | Pre | 5 | 0 | 0 | 1 | 0 | 4 | 0 | 0 | 0 | 0 | 0 | 0 | 0 | 0 | 0 | 0 | 0 | 0 |
| | Post | 5 | 0 | 0 | 0 | 0 | 0 | 2 | 1 | 1 | 1 | 0 | 0 | 0 | 0 | 0 | 0 | 0 | 0 |
| 4 | Pre | 5 | 4 | 2 | 0 | 2 | 4 | 3 | 3 | 3 | 3 | 3 | 1 | 3 | 4 | 3 | 5 | 5 | 3 |
| | Post | 5 | 4 | 5 | 4 | 4 | 5 | 5 | 4 | 3 | 5 | 5 | 1 | 3 | 3 | 4 | 5 | 5 | 5 |
| | Pre | 1 | 0 | 1 | 0 | 0 | 2 | 0 | 1 | 2 | 2 | 1 | 0 | 0 | 0 | 0 | 2 | 4 | 1 |
| | Post | 1 | 1 | 3 | 3 | 2 | 1 | 4 | 3 | 1 | 5 | 4 | 0 | 0 | 0 | 0 | 4 | 4 | 4 |
| 5 | Pre | 5 | 2 | 1 | 0 | 0 | 5 | 2 | 4 | 3 | 1 | 4 | 1 | 1 | 0 | 1 | 2 | 1 | 1 |
| | Post | 5 | 5 | 5 | 1 | 5 | 5 | 5 | 5 | 5 | 5 | 5 | 3 | 4 | 4 | 4 | 5 | 5 | 5 |
| | Post | 1 | 4 | 5 | 4 | 1 | 5 | 5 | 5 | 5 | 5 | 5 | 2 | 2 | 2 | 1 | 5 | 5 | 5 |
| 7 | Pre | 5 | 2 | 1 | 1 | 0 | 5 | 0 | 2 | 4 | 1 | 3 | 0 | 0 | 0 | 0 | 1 | 1 | 0 |
| | Post | 5 | 5 | 5 | 5 | 3 | 5 | 5 | 5 | 5 | 5 | 5 | 3 | 4 | 4 | 5 | 5 | 5 | 5 |
| | Post | 1 | 5 | 5 | 5 | 1 | 5 | 5 | 5 | 5 | 5 | 5 | 0 | 3 | 3 | 1 | 5 | 4 | 5 |
| 8 | Pre | 5 | 1 | 0 | 0 | 0 | 0 | 0 | 2 | 3 | 0 | 3 | 0 | 0 | 0 | 0 | 0 | 0 | 0 |
| | Post | 5 | 5 | 5 | 5 | 3 | 5 | 5 | 5 | 5 | 5 | 5 | 1 | 4 | 4 | 4 | 5 | 5 | 5 |
| | Post | 1 | 5 | 5 | 5 | 1 | 5 | 5 | 5 | 5 | 5 | 5 | 0 | 4 | 3 | 3 | 4 | 5 | 5 |
| 9 | Pre | 5 | 3 | 1 | 0 | 0 | 5 | 3 | 3 | 4 | 0 | 4 | 0 | 0 | 0 | 0 | 4 | 0 | 3 |
| | Post | 5 | 5 | 5 | 5 | 3 | 5 | 5 | 5 | 5 | 5 | 5 | 2 | 3 | 3 | 4 | 4 | 4 | 5 |

TABLE 6-continued

| Compound No. | Pre or Post Emergence | Rate kg/ hectare | Sb | Rp | Ct | P | Sn | Ip | Am | Pa | Ca | Po | Mz | Br | Rc | Ot | Dg | El | Pn |
|---|---|---|---|---|---|---|---|---|---|---|---|---|---|---|---|---|---|---|---|
|  | Post | 1 | 4 | 5 | 5 | 1 | 5 | 5 | 5 | 5 | 5 | 5 | 2 | 3 | 4 | 3 | 4 | 5 | 5 |
| 10 | Pre | 5 | 5 | 2 | 0 | 1 | 4 | 1 | 1 | 3 | 2 | 4 | 0 | 2 | 0 | — | 0 | 0 | 1 |
|  | Post | 5 | 5 | 4 | 5 | — | 5 | 5 | 5 | 5 | 5 | 5 | 3 | 3 | 3 | 4 | 5 | 5 | 5 |
| 11 | Pre | 5 | 4 | 0 | 0 | 3 | 4 | 0 | 0 | 0 | 3 | 2 | 1 | 1 | 0 | — | 0 | 0 | 1 |
|  | Post | 5 | 5 | 4 | 5 | — | 5 | 5 | 5 | 5 | 5 | 5 | 3 | 3 | 3 | 4 | 5 | 5 | 5 |
| 12 | Pre | 5 | 4 | 0 | 0 | 0 | 4 | 0 | 0 | 4 | 2 | 2 | 0 | 2 | 1 | — | 0 | 0 | 1 |
|  | Post | 5 | 5 | 4 | 5 | — | 5 | 5 | 5 | 5 | 5 | 5 | 1 | 0 | 2 | 1 | 5 | 4 | 4 |
| 16 | Pre | 5 | 4 | 0 | 0 | 0 | 5 | 1 | 2 | 3 | 3 | 0 | 0 | 0 | 0 | 2 | 0 | 0 | 0 |
|  | Post | 5 | 5 | 4 | 3 | 1 | 5 | 5 | 5 | 4 | 5 | 5 | 0 | 2 | 2 | 3 | 2 | 2 | 5 |
| 17 | Pre | 5 | 5 | 0 | 0 | 3 | 4 | 0 | 0 | 0 | 3 | 1 | 0 | 2 | 3 | 1 | 4 | 1 | 3 |
|  | Post | 5 | 3 | 0 | 0 | 2 | 4 | 0 | 0 | 1 | 0 | 2 | 0 | 0 | 0 | 0 | 0 | 0 | 1 |
| 18 | Pre | 5 | 4 | 5 | 4 | 3 | 5 | 5 | 5 | 5 | 5 | 5 | 2 | 4 | 0 | 5 | 5 | 5 | 4 |
|  | Post | 5 | 4 | 5 | 5 | 3 | 5 | 4 | 5 | 4 | 5 | 5 | 1 | 2 | 2 | 2 | 3 | 3 | 4 |
| 19 | Pre | 5 | 5 | 4 | 1 | 1 | 4 | 4 | 4 | 3 | 3 | 3 | 0 | 1 | 0 | 3 | 2 | 2 | 1 |
|  | Post | 5 | 3 | 5 | 4 | 3 | 4 | 4 | 3 | 4 | 5 | 5 | 0 | 1 | 0 | 0 | 0 | 0 | 3 |
| 20 | Pre | 5 | 5 | 4 | 3 | 3 | 5 | 4 | 5 | 5 | 3 | 5 | 0 | 1 | 0 | 4 | 3 | 3 | 2 |
|  | Post | 5 | 3 | 4 | 5 | 3 | 5 | 4 | 4 | 4 | 5 | 5 | 0 | 1 | 1 | 1 | 2 | 2 | 3 |
| 26 | Pre | 5 | 5 | 5 | 4 | 4 | 5 | 5 | 5 | 5 | 5 | 5 | 3 | 5 | 4 | 5 | 5 | 5 | 5 |
|  | Post | 5 | — | 4 | 4 | 3 | 4 | 4 | 5 | 4 | 5 | 5 | 2 | 2 | 2 | 3 | 5 | 3 | 5 |
| 27 | Pre | 5 | 5 | 5 | 4 | 3 | 5 | 4 | 5 | 5 | 4 | 5 | 0 | 3 | 3 | 5 | 5 | 4 | 5 |
|  | Post | 5 | — | 5 | 4 | 5 | 5 | 5 | 5 | 4 | 5 | 5 | 1 | 2 | 1 | 2 | 4 | 3 | 4 |
| 28 | Pre | 5 | 5 | 3 | 4 | 4 | 4 | 1 | 0 | 5 | 4 | 3 | 0 | 4 | 3 | 5 | 4 | 0 | 5 |
|  | Post | 5 | 5 | 5 | 5 | 4 | 5 | 5 | — | — | 5 | 5 | 0 | 0 | 1 | 1 | 3 | 2 | 4 |
| 29 | Pre | 5 | 5 | 0 | 4 | 3 | 2 | 0 | 0 | 4 | 0 | 1 | 0 | 3 | 3 | 5 | 4 | 0 | 3 |
|  | Post | 5 | 5 | 4 | 0 | 3 | 5 | 2 | — | — | 5 | 5 | 0 | 0 | 1 | 0 | 3 | 0 | 3 |
| 30 | Pre | 5 | 5 | 3 | 0 | 1 | 1 | 2 | 0 | 4 | 4 | 5 | 2 | 1 | 0 | 4 | 4 | 5 | 4 |
|  | Post | 5 | 4 | — | 2 | 5 | 5 | 5 | 4 | 5 | 5 | 2 | 1 | 4 | 4 | 5 | 5 | 5 | 5 |
| 31 | Pre | 5 | 5 | 4 | 3 | 2 | 3 | 4 | 5 | 3 | 5 | 5 | 1 | 1 | 0 | 4 | 2 | 3 | 4 |
|  | Post | 5 | 2 | 4 | 2 | 1 | 4 | 4 | 4 | 2 | 4 | 3 | 0 | 1 | 2 | 2 | 0 | 1 | 2 |
| 35 | Pre | 5 | 5 | 3 | 0 | 1 | 5 | 2 | 2 | 4 | 5 | 0 | 0 | 0 | 0 | 1 | 3 | 3 | 3 |
|  | Post | 5 | 5 | 4 | 3 | 2 | 5 | 4 | 0 | 4 | 5 | 0 | 3 | 4 | 3 | 5 | 5 | 5 | 5 |
| 39 | Pre | 5 | 1 | 2 | 0 | 0 | 2 | 1 | 1 | 2 | 2 | 1 | 0 | 0 | 0 | 0 | 3 | 2 | 1 |
|  | Post | 5 | 4 | 5 | 2 | 0 | 4 | 5 | 4 | 2 | 5 | 5 | 0 | 0 | 0 | 0 | 4 | 5 | 3 |
| 40 | Post | 5 | 3 | 5 | 4 | 0 | 5 | 5 | 5 | 3 | 5 | 5 | 0 | 0 | 0 | 0 | 1 | 2 | 3 |
|  | Post | 1 | 0 | 5 | 3 | 0 | 4 | 5 | 5 | 3 | 4 | 4 | 0 | 0 | 0 | 0 | 0 | 1 | 3 |
| 42 | Pre | 5 | 0 | 0 | 0 | 1 | 0 | 1 | 2 | 2 | 0 | 0 | 0 | 0 | 0 | 0 | 0 | 0 | 0 |
|  | Post | 5 | 4 | 5 | 5 | 0 | 5 | 5 | 5 | 5 | 5 | 5 | 0 | 0 | 2 | 3 | 4 | 4 | 4 |
| 43 | Post | 5 | 3 | 4 | 2 | 0 | 4 | 5 | 4 | 4 | 4 | 2 | 3 | 0 | 0 | 0 | 0 | 2 | 1 |
|  | Post | 1 | 0 | 0 | 0 | 0 | 0 | 1 | 1 | 1 | 0 | 0 | 0 | 0 | 0 | 0 | 0 | 0 | 0 |
| 44 | Post | 5 | 5 | 5 | 5 | 0 | 5 | 5 | 5 | 5 | 5 | 5 | 4 | 1 | 0 | 2 | 3 | 4 | 4 |
|  | Post | 1 | 5 | 5 | 5 | 1 | 5 | 5 | 5 | 5 | 5 | 5 | 3 | 1 | 0 | 0 | 1 | 4 | 4 |
| 45 | Post | 5 | 4 | 5 | 1 | 1 | 3 | 5 | 3 | 4 | 5 | 4 | 0 | 1 | 0 | 2 | 3 | 1 | 4 |
| 49 | Pre | 5 | 1 | 2 | 0 | 1 | 2 | 2 | 1 | 3 | 3 | 2 | 0 | 0 | 0 | 1 | 3 | 1 | 1 |
|  | Post | 5 | 4 | 5 | 5 | 3 | 5 | 5 | 5 | 4 | 5 | 5 | 0 | 0 | 0 | 1 | 5 | 5 | 4 |
| 50 | Pre | 5 | 2 | 2 | 0 | 0 | 2 | 2 | 1 | 2 | 3 | 2 | 0 | 0 | 0 | 1 | 1 | 1 | 0 |
|  | Post | 5 | 4 | 5 | 3 | 1 | 3 | 5 | 5 | 3 | 5 | 5 | 0 | 1 | 2 | 1 | 5 | 5 | 4 |
| 51 | Pre | 5 | 0 | 0 | 0 | 0 | 0 | 0 | 3 | 4 | 0 | 1 | 0 | 0 | — | 0 | — | — | 0 |
|  | Post | 5 | 5 | 5 | 5 | 0 | 5 | 5 | 5 | 5 | 5 | 5 | 5 | 2 | 1 | 0 | 1 | 4 | 3 |
| 52 | Post | 5 | 3 | 4 | 4 | 0 | 4 | 5 | 5 | 4 | 5 | 5 | 2 | 0 | 0 | 0 | 0 | 3 | 3 |
|  | Post | 1 | 0 | 3 | 0 | 0 | 1 | 4 | 3 | 3 | 3 | 4 | 0 | 0 | 0 | 0 | 0 | 1 | 0 |
| 53 | Pre | 5 | 0 | 0 | 0 | 0 | — | 0 | 0 | 0 | 0 | 0 | 0 | 0 | 0 | 0 | 0 | 0 | 0 |
|  | Post | 5 | 3 | 3 | 2 | 1 | 4 | 3 | 1 | 3 | 5 | 4 | 0 | 0 | 1 | 0 | 2 | 2 | 1 |
| 54 | Pre | 5 | 4 | 4 | 0 | 0 | 4 | 3 | 0 | 2 | 4 | 4 | 0 | 0 | 0 | 0 | 1 | 1 | 2 |
|  | Post | 5 | 4 | 4 | 4 | 4 | 5 | 5 | 5 | 3 | 5 | 5 | 0 | 0 | 2 | 2 | 3 | 3 | 3 |
| 55 | Pre | 5 | 5 | 5 | 2 | 2 | 4 | 5 | 5 | 4 | 2 | 5 | 1 | 3 | 4 | 4 | 4 | 4 | 5 |
|  | Post | 5 | 2 | 4 | 2 | 2 | 5 | 4 | 4 | 3 | 4 | 4 | 0 | 1 | 1 | 2 | 3 | 3 | 4 |

A dash (—) in the above table means that no test was carried out.

EXAMPLE 13

This Example illustrates the selective herbicidal activity of compounds according to the invention. The compounds were tested by the methods previously described in Example 12. For comparison, the results of tests carried out with a related compound previously proposed for use as a herbicide in Belgian Pat. No. 799,932 are included. The comparison compound was the compound of the following formula:

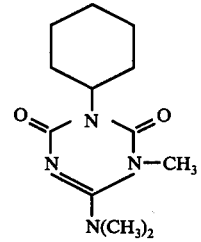

This compound is referred to as compound A in the table of results below. In this table, the results quoted are those for post-emergence tests. Damage to plants is expressed on a scale of 0 to 9 where 0 is no effect and 9 is complete kill. It will be seen that the compounds of the invention are relatively nontoxic towards maize at rates which cause severe damage to the other plant species.

TABLE 7

| Compound No. | Rate/ Kg/Ha | Test Plants | | | | | | | | | | | |
|---|---|---|---|---|---|---|---|---|---|---|---|---|---|
| | | Mz | Rc | Sg | Sy | Gn | Ct | Ei | Ec | St | Dg | Po | Am |
| A | 0.5 | 9 | 9 | 9 | 9 | 9 | 9 | 9 | 9 | 9 | 9 | 9 | 9 |
| 4 | 2 | 0 | 7 | 7 | 8 | 9 | 9 | 9 | 8 | 9 | 9 | 9 | 9 |
| 5 | 2 | 0 | 7 | 7 | 8 | 9 | 9 | 9 | 9 | 9 | 9 | 9 | 9 |
| 7 | 2 | 0 | 5 | 7 | 9 | 9 | 9 | 9 | 8 | 9 | 9 | 9 | 9 |
| 8 | 2 | 1 | 6 | 6 | 9 | 7 | 9 | 9 | 9 | 9 | 9 | 9 | 9 |
| 9 | 2 | 2 | 0 | 5 | 9 | 8 | 9 | 9 | 9 | 9 | 9 | 9 | 9 |
| 10 | 1 | 0 | 6 | 6 | 8 | 5 | 8 | 7 | 7 | 5 | 7 | 9 | 9 |
| 11 | 1 | 0 | 6 | 7 | 9 | 4 | 8 | 7 | 9 | 7 | 7 | 9 | 9 |
| 12 | 2 | 0 | 1 | 1 | 0 | 3 | 3 | 5 | 6 | 6 | 5 | 9 | 9 |
| 28 | 2 | 1 | 3 | 3 | 9 | 8 | 6 | 2 | 8 | 2 | 1 | 9 | 9 |
| 29 | 2 | 0 | 5 | 1 | 9 | 9 | 6 | 0 | 5 | 1 | 0 | 9 | 6 |
| 42 | 2 | 0 | 2 | 5 | 9 | 8 | 9 | 8 | 4 | 9 | 9 | 9 | 9 |
| 43 | 2 | 2 | 6 | 8 | 9 | 8 | 9 | 9 | 9 | 9 | 9 | 9 | 9 |

The names of the test plants are as follows:-

- Mz - Maize
- Rc - Rice
- Sg - Sorghum
- Sy - Soya Bean
- St - Setaria viridis
- Dg - Digitaria sanguinalis
- Gn - Groundnut
- Ct - Cotton
- Ei - Eleusine indica
- Ec - Echinochloa crus-galli
- Po - Portulaca oleracea
- Am - Amaranthus retroflexus

EXAMPLE 14

This Example illustrates the fungicidal properties of compounds according to the invention. The compounds were tested against a wide variety of foliar fungal diseases of plants. In the test, a composition comprising an aqueous solution or suspension of the test compound was sprayed on to the foliage or uninfected plants; the soil in which the plants were growing was also drenched with the composition. The compositions used for spraying and drenching contained 100 parts per million (ppm.) of the test compound except where otherwise stated in the table of results below. After spraying and drenching, the plants were then exposed to infection with the diseases it was desired to control, along with control plants not treated with the compound. After a period of days, depending upon the particular disease, the extent of the disease was visually assessed, as a percentage of the disease established upon the control plants which had not been treated with the compound under test, according to the grading scheme below:

| Grading | Amount of disease as a percentage of disease on control plants |
|---|---|
| 0 | 61 to 100 |
| 1 | 26 to 60 |
| 2 | 6 to 25 |
| 3 | 0 to 5 |

In Table 8 below the name of the disease is given in the first column, and in the second column is given the time which elapsed between exposing the plants to infection and assessing the amount of disease. Table 9 gives the test results.

TABLE 8

| Disease and Plant | Time Interval (days) | Disease Code Letter (Table 9) |
|---|---|---|
| Phytophthora infestans (tomato) | 3 | A |
| Plasmopara viticola (vine) | 7 | B |
| Uncinula necator (vine) | 10 | C |
| piricularia oryzae (rice) | 7 | D |
| Podosphaera leucotricha (apple) | 10 | E |
| Puccinia recondita (wheat) | 10 | F |
| Erysiphegraminis (barley) | 10 | G |

TABLE 9

| Compound No. | A | B | C | D | E | F |
|---|---|---|---|---|---|---|
| 3 | 0–1 | 0 | 4 | 0 | 4 | 0 |
| 4 | 0 | 2–3 | 4,P | 0 | 3,P | 0,P |
| 5 | P | 3,P | 3,P | 0,P | P | 2 |
| 8 | P | — | — | 0 | P | 3 |
| 9 | P | — | — | 0 | P | 3 |
| 10 | P | P | P | 0 | P | 4 |
| 11 | P | P | P | 1 | P | 4 |
| 12 | P | P | P | 3,P | 3,P | 4 |
| 13 | 0,P | 2–3P | 4 | 0 | 4 | 0 |
| 14 | 0 | 0–1 | 2–3 | 2–3 | 3 | 0 |
| 15 | 0 | 0 | 4 | 2 | 4 | 0 |
| 16 | P | 3 | 4 | 0,P | 4 | 0 |
| 18 | P | P | 3–4 | P | P | 3 |
| 19* | P | P | 2–3 | P | P | 2 |
| 20* | P | 4,P | 2–3 | P | P | 2 |
| 23* | 3 | 0–1 | 3–4 | 3 | 4 | 0 |
| 24* | 3 | 0–1 | 4 | 0 | 4 | 0 |
| 26* | P | 3–4 | — | P | P | 4 |
| 27* | P | 4,P | — | 4 | P | 4 |
| 31* | 1 | 3 | — | 0 | 0 | 2 |
| 32 | 0–2 | 0 | — | P | 3,4 | 0 |
| 36 | P | 3 | — | P | 4 | 3 |
| 37* | P | 3 | — | P | 4 | 3 |
| 47 | 2 | 0 | 3–4 | 0 | 0 | 0 |
| 50 | 0,P | P | 4,P | P | 0 | 0,P |
| 52 | P | P | P | 0 | P | 4 |
| 53* | 0 | — | — | 0 | 4 | 0 |
| 54 | 1 | 2 | 0 | — | — | 0 |
| 56 | 3 | 0 | 0–3 | 0 | 0 | 0 |
| 57 | P | 0–3 | 4,P | 0 | 0 | 0 |
| 60 | P | 0–2 | 0 | 0 | 0 | |
| 61 | 0 | 0 | 4 | 0 | 4 | 0 |
| 62* | P | 4 | — | P | P | 3 |
| 63* | P | 4 | — | P | 4 | 4 |
| 64 | P | 4 | — | 0 | 2,P | 3 |

Compounds marked with an asterisk * were tested at 200 parts per million.

EXAMPLE 15

This Example illustrates the fungicidal activity of certain compounds of the invention at lower rates on powdery mildew of barley in comparison with a commercial standard.

The technique used was that of Example 14 but separate testes were carried out for protectant (PF), eradicant (EF) and translocated (TF) fungicidal activity. In the protectant tests, the plants were sprayed 1-2 days before inoculation with the disease; in the eradicant test, the plants were inoculated 1–2 days before spraying; in the translocated activity test, the soil was drenched 1–2 days before inoculation. Assessment was carried out as in Example 14 after the periods indicated in the Example, and the results are indicated by the same code in Table 10

TABLE 10

| Test Compound | (Rate of Application ppm.) | | | | | | | | | | | |
|---|---|---|---|---|---|---|---|---|---|---|---|---|
| | 50 | | | 25 | | | 10 | | | 5 | | |
| | PF | EF | TF | PF | EF | TF | PF | EF | TF | PF | EF | TF |
| 13 | | | 3–4 | 0–2 | | 2–4 | 0 | | 0–3 | 0–1 | | |
| 53 | | | 4 | 1–2 | | 4 | 0 | | 3–4 | 0 | | |
| Ethirimol | 3–4 | 3–4 | 3 | | 3–4 | 1–2 | | 3 | 2 | | | |

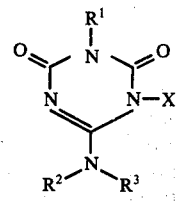

EXAMPLE 16

This Example illustrates the activity of some of the compounds of our invention against plant bacterial diseases. Compounds from Tables 1 and 2 were tested against *Pseudomonas tomato* and *Xanthomonas oryzae*. Results are given in Table 11 below.

Test Procedure for *Pseudomonas tomato*

Tomato seedlings grown in 2 inch pots were treated with a root drench (10 ml.) containing 200 ppm. of the chemical compounds under test. Twenty-four hours later the seedlings were inoculated with *Pseudomonas tomato* by applying a suspension of cells of this bacterium to wounds made in the seedlings.

After three weeks the condition of the tomato seedlings was assessed on a 0–4 scale; where 0 is no control, 1 is slight control, 2 is fair control, 3 is good control and 4 is complete control.

Test Procedure for *Xanthomonas oryzae* (Bacterial Blight of Rice)

Rice seedlings at the three leaf stage were root drenched (10 ml.) and sprayed to run-off with the chemical compound under test at a rate of 200 ppm. Twenty-four hours later, the plants were inoculated by wounding with forceps dipped in a suspension of *Xanthomonas oryzae* spores. After fourteen days at 100% relative humidity the seedlings were assessed for disease on the 0–4 scale described above.

TABLE 11

| Compound No. (of Tables 1–2) | DISEASE | |
|---|---|---|
| | *Xanthomonas oryzae* | *Pseudomonas tomato* |
| 1 | 2 | |
| 2 | 1–2 | |
| 39 | 2 | 3 |
| 49 | | 3 |
| 50 | | 3 |
| 52 | 2–3 | 0–1 |

The compounds in the above table tended to cause some damage to the test plants, although this was less marked with compound 52.

I claim:

1. A process of inhibiting the growth of unwanted plants, which comprises applying to plants, or to a plant growth medium, a phytotoxic amount of a triazine-dione compound of the formula:

wherein $R^1$ is an alkyl radical of 1 to 8 carbon atoms and either (a) $R^2$ is a carboxylic acyl radical of formula $R^4$.CO— wherein $R^4$ is a carboxy group, an alkoxycarbonyl group, an alkoxy group of 1 to 6 carbon atoms, an alkyl group of 1 to 6 carbon atoms, or a phenyl radical and $R^3$ is a hydrogen atom or an alkyl radical of 1 to 6 carbon atoms, or (b) $R^2$ is a hydrogen atom or an alkyl radical of 1 to 6 carbon atoms and $R^3$ together with the group X, forms a divalent radical Z linking the exocyclic nitrogen atom to which $R^3$ is attached to the nitrogen atom in the triazine ring, so as to form a second 5- or 6-membered ring, the radical Z being selected from the group consisting of oxalyl (—CO.CO—), 1,2-dihydroxyethylene (—CH(OH)—CH(OH)—), and radicals of the formula —CH$_2$NR$^5$CH$_2$— wherein $R^5$ is phenyl, an alkyl group of 1 to 10 carbon atoms or hydrogen; and X is a hydrogen atom, a salt-forming cation comprising an alkali metal, an alkaline earth metal, ammonia, or a primary, secondary, or tertiary alkyl amine in which the alkyl contains 1 to 6 carbon atoms, or an alkyl radical of 1 to 6 carbon atoms, or together with $R^3$ forms the divalent group Z.

2. A process according to claim 1 wherein the rate of application of the triazine-dione compound is from 0.1 to 10 kilograms per hectare.

3. A process of inhibiting the growth of weeds in crops of maize, which comprises applying to the crop area an effective amount of a triazine-dione compound having the formula:

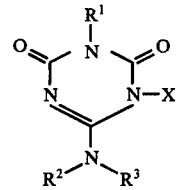

in an amount sufficient to inhibit the growth of weeds, but insufficient substantially to damage the maize wherein $R^1$ is an alkyl radical of 1 to 8 carbon atoms and either (a) $R^2$ is a carboxylic acyl radical of formula $R^4$.CO— wherein $R^4$ is a carboxy group, an alkoxycarbonyl group, an alkoxy group of 1 to 6 carbon atoms, an alkyl group of 1 to 6 carbon atoms, or a phenyl radical and $R^3$ is a hydrogen atom or an alkyl radical of 1 to 6 carbon atoms, or (b) $R^2$ is a hydrogen atom or an alkyl radical of 1 to 6 carbon atoms and $R^3$ together with the group X, forms a divalent radical Z linking the exocyclic nitrogen atom to which $R^3$ is attached to the nitrogen atom in the triazine ring, so as to form a second 5- or 6-membered ring, the radical Z being selected from the group consisting of oxalyl (—CO.CO—), 1,2-dihydroxyethylene (—CH(OH)—CH(OH)—), and radicals of the formula —CH$_2$NR$^5$CH$_2$— wherein $R^5$ is phenyl, an alkyl group of 1 to 10 carbon atoms or hydrogen; and X is a hydrogen atom, a salt-forming cation comprising an alkali metal, an alkaline earth metal, ammonia, or a primary, secondary, or tertiary alkyl amine in which the alkyl contains 1 to 6 carbon atoms, or an alkyl radical of 1 to 6 carbon atoms, or together with $R^3$ forms the divalent group Z.

4. A herbicidal composition, comprising a herbicidally effective amount of a triazine-dione compound of the formula:

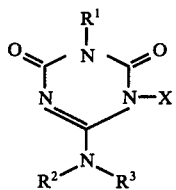

in admixture with a carrier comprising a solid or liquid diluent, wherein $R^1$ is an alkyl radical of 1 to 8 carbon atoms and either (a) $R^2$ is a carboxylic acyl radical of formula $R^4$.CO— wherein $R^4$ is a carboxy group, an alkoxycarbonyl group, an alkoxy group of 1 to 6 carbon atoms, an alkyl group of 1 to 6 carbon atoms, or a phenyl radical and $R^3$ is a hydrogen atom or an alkyl radical of 1 to 6 carbon atoms, or (b) $R^2$ is a hydrogen atom or an alkyl radical of 1 to 6 carbon atoms and $R^3$ together with the group X, forms a divalent radical Z linking the exocyclic nitrogen atom to which $R^3$ is attached to the nitrogen atom in the triazine ring, so as to form a second 5- or 6-membered ring, the radical Z being selected from the group consisting of oxalyl (—CO.CO—), 1,2-dihydroxyethylene (—CH(OH)—CH(OH)—), and radicals of the formula —CH$_2$NR$^5$CH$_2$— wherein $R^5$ is phenyl, an alkyl group of 1 to 10 carbon atoms or hydrogen; and X is a hydrogen atom, a salt-forming cation comprising an alkali metal, an alkaline earth metal, ammonia, or a primary, secondary, or tertiary alkyl amine in which the alkyl contains 1 to 6 carbon atoms or an alkyl radical of 1 to 6 carbon atoms, or together with $R^3$ forms the divalent group Z.

5. A composition according to claim 4, which further comprises a surface-active agent.

* * * * *